(12) United States Patent
Qiu

(10) Patent No.: US 10,306,928 B2
(45) Date of Patent: Jun. 4, 2019

(54) REPLACEABLE UNIVERSAL ATOMIZING HEAD, ATOMIZER, AND ELECTRONIC CIGARETTE WITH ATOMIZING HEAD

(71) Applicant: JOYETECH EUROPE HOLDING GMBH, Zug (CH)

(72) Inventor: Wei-Hua Qiu, ChangZhou (CN)

(73) Assignee: JOYETECH EUROPE HOLDING GMBH, Zug (CH)

(*) Notice: Subject to any disclaimer, the term of this patent is extended or adjusted under 35 U.S.C. 154(b) by 314 days.

(21) Appl. No.: 15/279,443

(22) Filed: Sep. 29, 2016

(65) Prior Publication Data

US 2017/0013885 A1    Jan. 19, 2017

Related U.S. Application Data

(63) Continuation-in-part of application No. 13/695,544, filed on Oct. 19, 2011, now abandoned.

(30) Foreign Application Priority Data

Sep. 28, 2011 (CN) .......................... 2011 1 0302179

(51) Int. Cl.
    *A24F 47/00* (2006.01)
    *A61M 11/04* (2006.01)

(52) U.S. Cl.
    CPC ......... *A24F 47/008* (2013.01); *A61M 11/042* (2014.02)

(58) Field of Classification Search
    CPC .. A24F 47/008; A61M 11/041; A61M 11/042; A61M 11/06; A61M 15/06;
    (Continued)

(56) References Cited

U.S. PATENT DOCUMENTS 4,195,044 A * 3/1980 Miller .................... A61M 11/06
                                                    128/200.18
4,427,004 A * 1/1984 Miller .................... A61M 11/06
                                                    128/200.21
(Continued)

FOREIGN PATENT DOCUMENTS

CN      201072979 Y    6/2008
CN      101986906 A    3/2011
(Continued)

OTHER PUBLICATIONS

The office action of its parent U.S. Appl. No. 13/695,544, dated Aug. 12, 2014.
(Continued)

*Primary Examiner* — Annette Dixon
(74) *Attorney, Agent, or Firm* — ScienBiziP, P.C.

(57) ABSTRACT

An atomizing head for an electronic cigarette, the atomizing head being universal and replaceable, includes a support base defining an atomizing chamber, a heating device, and a liquid guiding member. The liquid guiding member includes a liquid guiding wick, a liquid guiding nozzle, and a liquid guiding nozzle seat. One end of the liquid guiding wick extends from the liquid guiding nozzle seat to the heating device. The nozzle and nozzle seat cooperatively define a receiving cavity, the receiving cavity is blocked by the liquid guiding wick, and an inner surface of the receiving cavity defines at least one liquid guiding slot for providing a channel for a liquid to the heating device. An atomizer and an electronic cigarette including the replaceable universal atomizing head are also described.

20 Claims, 12 Drawing Sheets

(58) Field of Classification Search
CPC .............. A61M 16/109; A61M 16/125; A61M 16/147; A61M 16/16; A61M 16/162; A61M 16/20; A61M 2016/0024; A61M 2202/0208; A61M 2205/3653; A61M 2205/42; A61M 2205/8206; H05B 3/0014; H05B 3/06; Y10S 261/65
See application file for complete search history.

(56) References Cited

U.S. PATENT DOCUMENTS

| | | | | |
|---|---|---|---|---|
| 4,911,157 | A | * | 3/1990 | Miller ................... A61M 16/16 128/200.21 |
| 5,894,841 | A | * | 4/1999 | Voges ................... A24F 47/008 128/203.12 |
| 6,196,218 | B1 | * | 3/2001 | Voges ................... A24F 47/002 128/200.14 |
| 2006/0196518 | A1 | * | 9/2006 | Hon ...................... A24F 47/002 131/360 |
| 2012/0111347 | A1 | * | 5/2012 | Hon ...................... A24F 47/008 131/329 |

FOREIGN PATENT DOCUMENTS

| | | |
|---|---|---|
| CN | 201781984 U | 4/2011 |
| WO | 2009/155734 A1 | 12/2009 |

OTHER PUBLICATIONS

The office action of its parent U.S. Appl. No. 13/695,544, dated Jan. 5, 2015.
The office action of its parent U.S. Appl. No. 13/695,544, dated Dec. 2, 2015.
The office action of its parent U.S. Appl. No. 13/695,544, dated Mar. 31, 2016.

* cited by examiner

REPLACEABLE UNIVERSAL ATOMIZING HEAD, ATOMIZER, AND ELECTRONIC CIGARETTE WITH ATOMIZING HEAD

CROSS-REFERENCE TO RELATED APPLICATIONS

The subject matter herein generally relates to an atomizing head. This application is a continuation-in-part application of U.S. patent application Ser. No. 13/695,544, filed Oct. 19, 2011, which claims priority to CN Patent Application Serial Number 201110302179.2, filed Sep. 28, 2011, the disclosure of which is incorporated herein by reference.

FIELD

The invention relates to an electronic cigarette, in particular to a replaceable universal atomizing head, an atomizer and an electronic cigarette.

BACKGROUND

The atomizer and the battery rod are two major components of the electronic cigarette. The battery rod consists of a PCB board, a rechargeable battery, and various other circuits; the atomizer consists of an atomizing device and a cartridge. The Application No. CN201878765U of a Utility Model Patent discloses an atomizer (see FIG. 12), wherein the atomization device of the atomizer includes a main body 330 of the atomizer, a suction nozzle seat 310, a heating device 311 and a liquid guiding component, wherein one end of the suction nozzle seat provides an atomizing chamber 313, the other end of the suction nozzle seat has a vent hole 314 which communicate with an atomizing chamber, wherein the heat means is fixed in the atomizing chamber; the liquid guiding component includes a suction nozzle and a liquid guiding rope 320. One end of the suction nozzle is inserted into the liquid storage cavity of a liquid storage box, wherein the contacting parts form a liquid seal and the other end of the suction nozzle connects with an atomizing chamber of the suction nozzle seat. The liquid guiding rope 320 is wound on the heat device 311 and both ends of the liquid guiding rope 320 are introduced into the suction nozzle.

A connecting assembly of the atomizing device 30 is fixed to the other end of the main body 330. The connecting assembly includes a main body 330 of the atomizer, a contacting conductor 331 connected to the heating device 311 by conductors, and a contacting conductor base 332. One end of the main body 330 of the atomizer located in the main body 330 forms a cavity for receiving and holding the atomizing assembly. The sleeve 312 and the other atomizing assemblies are fixed in the cavity, wherein the sleeve 312 cooperates with the cavity in a manner of interference fit. The sidewall of the main body of the atomizer is provided with an inlet hole 333 for conducting air which communicates with the cavity. The contacting conductor base 332 is fixed on the other end of the main body of the atomizer exposed from the main body 330, wherein two contacting conductors 331 are fixed in the contacting conductor base 332. The conductors 331 connect to the positive and negative terminals of a power supply, wherein each contacting conductor has a hole for contacting thimble accessing. Further, the outer surface of the main body 330 of the atomizer has a step, the main body 330 of the atomizer supports the atomizer assembly firstly, and connects to the power supply secondly.

The atomizing apparatus of the above-described structures can atomize the liquid, but also has the following disadvantages:

Firstly, the configuration of the atomizing device is a heating device. The heating is battery powered and evaporates the electronic cigarette liquid to form the smoke. Traditional electronic cigarette atomizer with the main body is a unibody, and the atomization device can be used only for a few days and cannot be replaced after damage. Also, the use cost is high. Smoke taste is degraded if a separate atomizing device is used for a long time, and the amount of smoke becomes smaller.

Secondly, the two contacting conductors 331 are a conductive positive electrode and a negative electrode, respectively. The electrically positive and the negative electrodes are welded to ends of the heat device 311. Since the outer diameter of the main body 330 of the atomizer is only 10 nm and the assembly of these parts is by hand, this is a manufacturing difficulty and increases the labor intensity.

Thirdly, since the concentration and density of the liquid itself is relatively high, the liquid guiding wick, which occupies space of the suction nozzle, results in very low flow rate of the liquid. On the other hand, when the liquid is flowing and being heated, the low flow speed of the liquid is slower than the operating speed of the heating apparatus, thus only a small portion of the liquid can reach the heating device. This does not meet the normally required proportion of liquid, and the gas in the mouth is very dry. This phenomenon is called dry combustion.

SUMMARY

The present disclosure provides a replaceable universal atomizing head that has a simple structure which is easy to assemble and can prevent dry combustion.

A replaceable universal atomizing head includes a support base defining an atomizing chamber, a heating device, the heating device mounted in the atomizing chamber of the support base, and a liquid guiding member. The liquid guiding member includes a liquid guiding wick, a liquid guiding nozzle, and a liquid guiding nozzle seat. The liquid guiding wick has two ends, the liquid guiding nozzle seat connects integrally with the liquid guiding nozzle. One end of the liquid guide wick extends from the liquid guiding nozzle seat and reaches the heating device, the other end of the liquid guide wick is inserted into the liquid guiding nozzle. The liquid guiding nozzle and the liquid guiding nozzle seat cooperatively to define a receiving cavity. The receiving cavity is blocked by the liquid guiding wick, the receiving cavity has an inner surface, and the inner surface defines at least one liquid guiding slot for providing a channel for a liquid to the heating device.

In the above arrangement, the support base is mounted in the middle of the conductive ring cavity so as to press hard on a wire connected to one end of the heating device between the conductive ring and the support base. Welding of the conductive cathode and the heating device is not required artificially, which can reduce process and labor intensity. A conductive member is fitted in the other end of the conductive ring cavity, so almost all parts of the universal atomizing head are mounted in the conductive ring. The entire structure of the universal atomizing head thus becomes simple and compact. Making the universal atomizing head of the disclosure, in comparison to making the existing atomizing head, can save 2-3 minutes, and the cost is three-fourths of that of the existing atomizing head. In terms of production time, labor intensity, and cost, the universal atomizing head of the present disclosure has great advantages. The wall surface of the inner hole of the liquid guiding nozzle and the liquid guiding nozzle seat provide a liquid guiding slot, such slot improves the flow rate of the liquid by providing a drain for the liquid. When being heated, the evaporation of the liquid is provided and the heating device is appropriate, so the phenomenon of dry combustion is avoided.

Another objective is to provide an atomizer which can be replaced after damage or after long-time use on the electronic cigarette, and is beneficial to reducing the use costs.

The universal atomizing head of the atomizer is replaceable. The atomizer further comprises an atomization assembly and a connector. The atomization assembly provides a space for accommodating the universal atomizing head and the universal atomizing head is detachably mounted in the space. The atomization assembly connects to the connector, and the universal atomizing head is in contact with the connector electronically.

The atomization assembly provides a universal receiving cavity for accommodating the universal atomizing head that is detachably mounted in the receiving cavity. When the performance of the universal atomizing head mounted in the receiving cavity becomes inefficient or unacceptable, the universal atomizing head can be removed from the receiving cavity, without replacing the atomizer overall, which helps to reduce the use cost.

An electronic cigarette, which has a universal atomizing head that can be replaced at any time, can reduce production cost.

An electronic cigarette is provided with the atomizer. The electronic cigarette further comprises a battery rod. The battery rod and the connector of the atomizer have threaded connections.

The atomizer of the disclosed electronic cigarette is more advantageous than the traditional atomizer previously described.

The drawings should be combined with specific embodiments to fully describe the structures and advantages of the disclosure.

BRIEF DESCRIPTION OF THE DRAWINGS

Implementations of the present technology will now be described, by way of example only, with reference to the attached figures.

Figure 1:
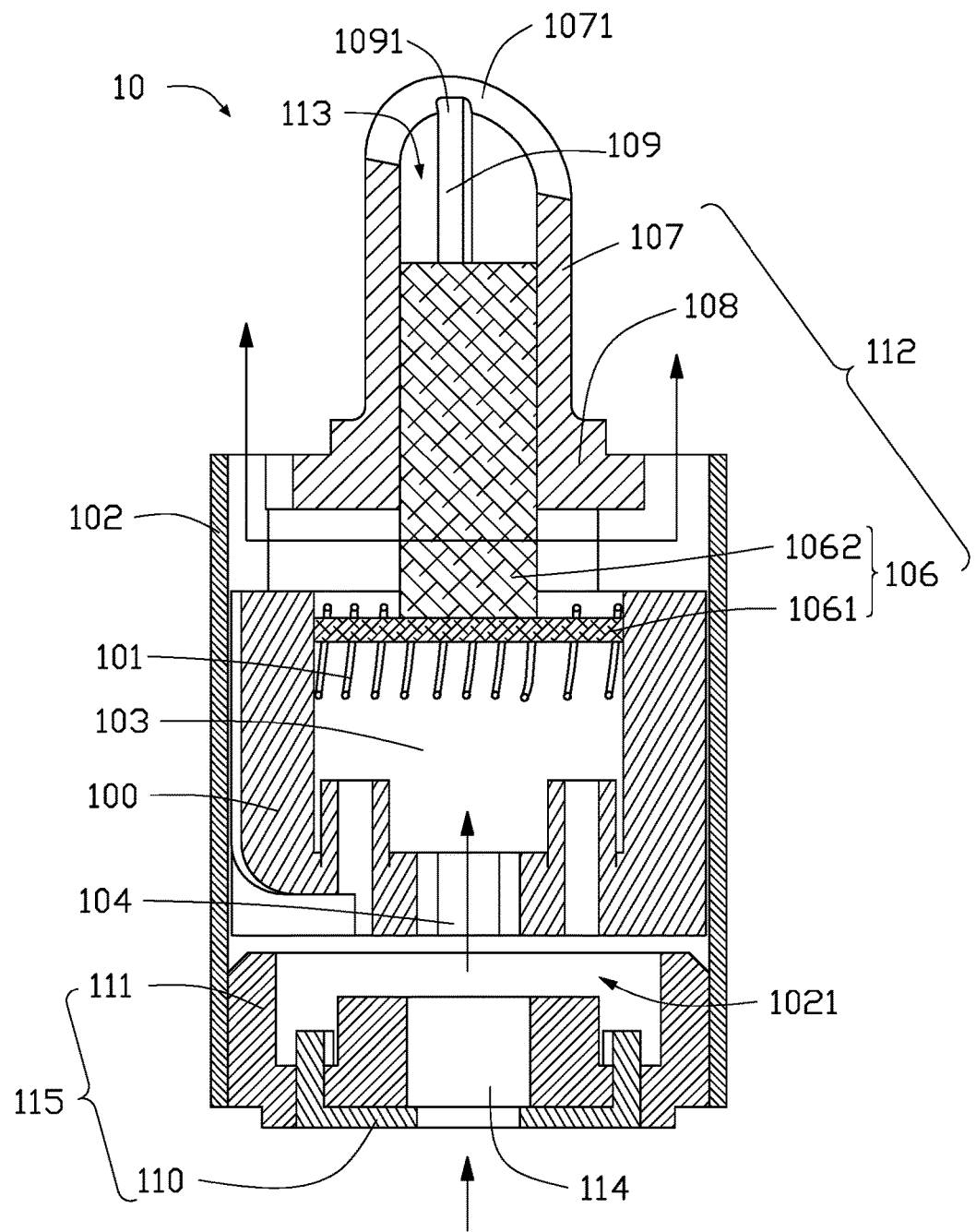
FIG. 1 is a cross-sectional structure view of a replaceable universal atomizing head, the atomizing head includes a liquid guiding wick and a heating device.

In the drawings, 10 is a universal atomizing head, 100 is a support base, 101 is a heating device, 102 is a conductive ring, 1021 is a receiving space, 103 is an atomizing chamber, 104 is a vent hole, 105 is a liquid absorbent member, 112 is a liquid guiding member, 106 is a liquid guiding wick, 1061 is a horizontal portion, 1062 is a vertical portion, 107 is a liquid guiding nozzle, 1071 is an inclined plane, 108 is a liquid guiding nozzle seat, 113 is a receiving cavity, 109 is a liquid guiding slot, 1091 is an inner surface, 110 is a conductor, 111 is an insulator, 114 is an air hole, and 115 is a conductive member.

20 is an atomizer, 21 is a connector, 22 is an atomization assembly, 221 is a space, 200 is a cartridge, 210 is a box, 220 is a spraying piece, 201 is a housing, 202 is a first sleeve, 2021 is a stepped bore, 203 is a small aperture section, 204 is a greater aperture section, 2040 is an annular retaining projection, 205 is an insulation sleeve, 206 is a sleeve, 207 is a conductive negative electrode, 208 is a conductive positive electrode, 209 is an insulating member, 210 is a notch, 211 is a screw, 212 is a circlip, and 213 is an alignment hole.

30 is an electronic cigarette, and 300 is a battery rod.

DETAILED DESCRIPTION

Figure 2:
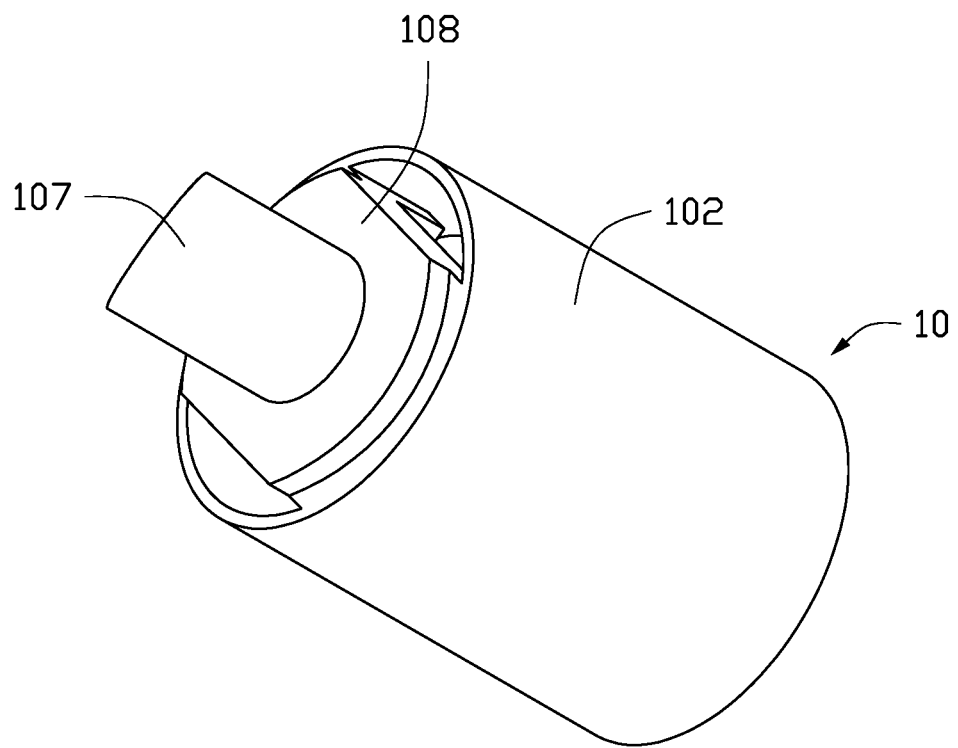
FIG. 2 is a perspective view of the atomizing head in FIG. 1.
Figure 3:
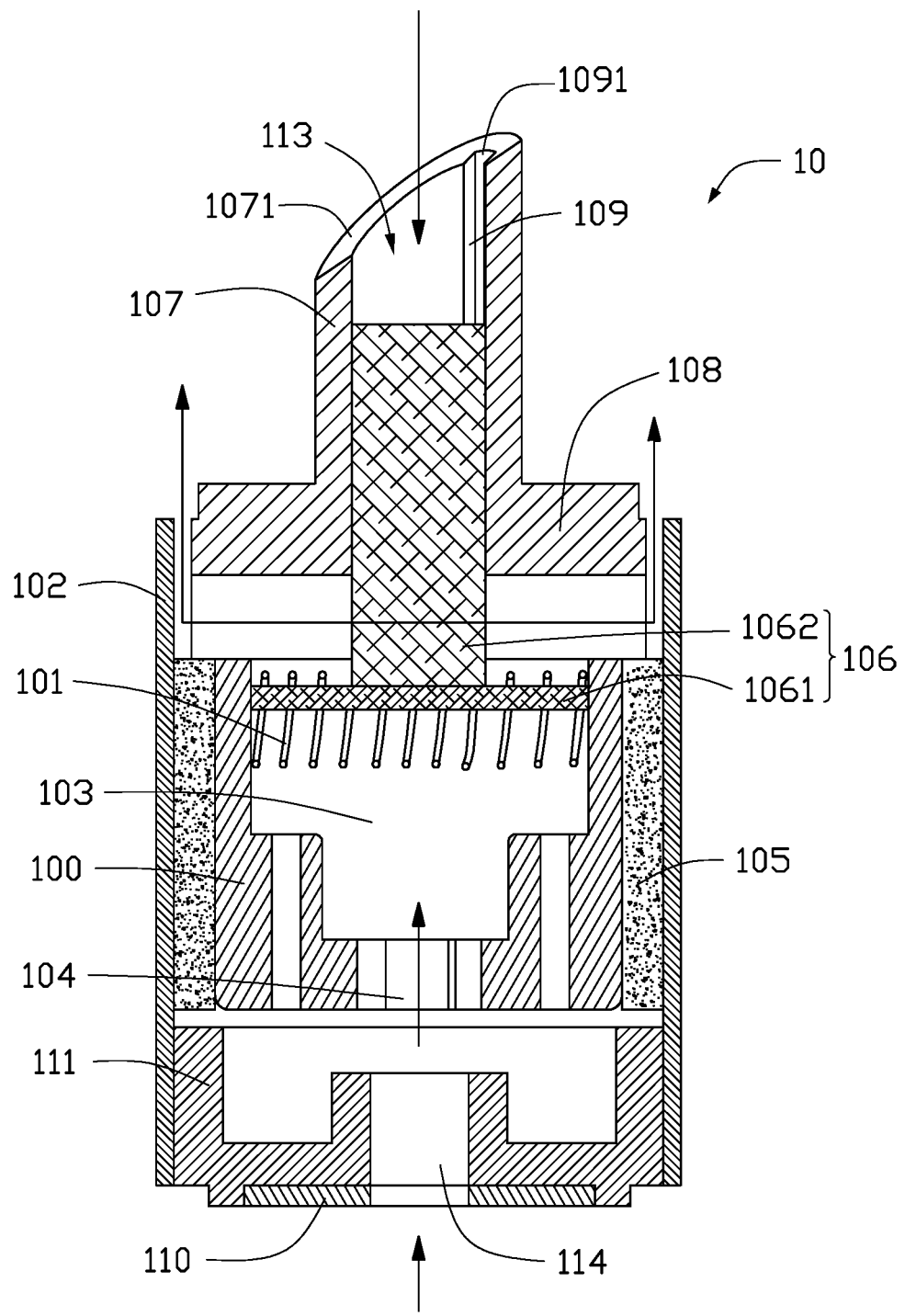
FIG. 3 is another cross-sectional structural view of the universal atomizing head similar to FIG. 1 including a liquid absorbing member.

Referring to FIGS. 1 to 3, a universal atomizing head 10 comprises a support base 100 defining an atomizing chamber 103, a heating device 101, a conductive ring 102, a liquid guiding member 112, and a conductive member 115. The support base 100 is made of ceramic, and the atomizing chamber 103 is provided in the ceramic support base 100. In order to permit a gas (or gases) to enter into the atomization chamber 103, a vent hole 104 is provided in the bottom of the support base 100. The heating device 101 is a heating wire made of metal, mounted on the atomizing chamber 103 of the support base 100. Before assembly, a plurality of wires is welded to both ends of the heating device 101. The conductive ring 102 is a negative conductor of the universal atomizing head 10, the conductive ring 102 is also used to mount other components.

Referring to FIG. 1, the conductive ring 102 defines a receiving space 1021, and the receiving space 1021 has two ends. The support base 100 is in the receiving space 1021 and mounted close to a middle portion of the conductive ring 102. A first wire connected to one end of the heating device 101 is between the conductive ring 102 and the support base 100, making the first wire and the conductive ring 102 maintain good contact, so that without welding the conductive cathode and the heating device 101 artificially, process and labor intensity can be reduced. Referring to FIG. 3, a layer of a liquid absorbing member 105 wraps the outer surface of the support base 100, in which the liquid absorbing member 105 is a nickel mesh, to reduce incidence of the liquid reflowing to the universal atomizing head 10. The support base 100 wrapped in the liquid absorbing member 105 is in the receiving space 1021 and mounted close to a middle portion of the conductive ring 102. The support base 100 also presses on a first wire that is connected to one end of the heating device 101 between the conductive ring 102 and the nickel mesh, so the first wire and the conductive ring 102 maintain good contact.

Figure 4:
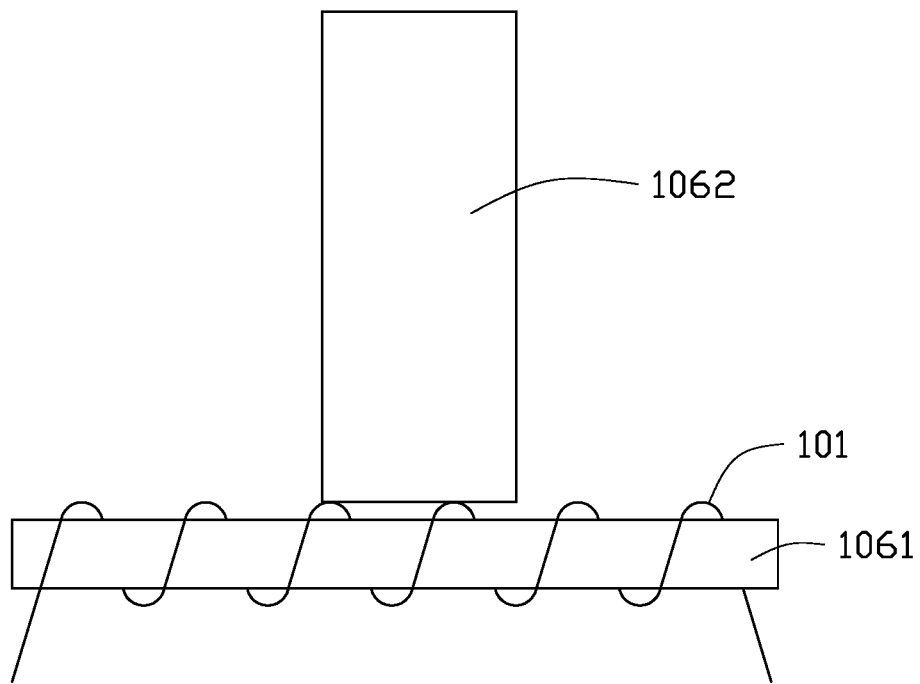
FIG. 4 is a perspective, enlarged view of the liquid guiding wick and the heating device in FIG. 1.
Figure 5:
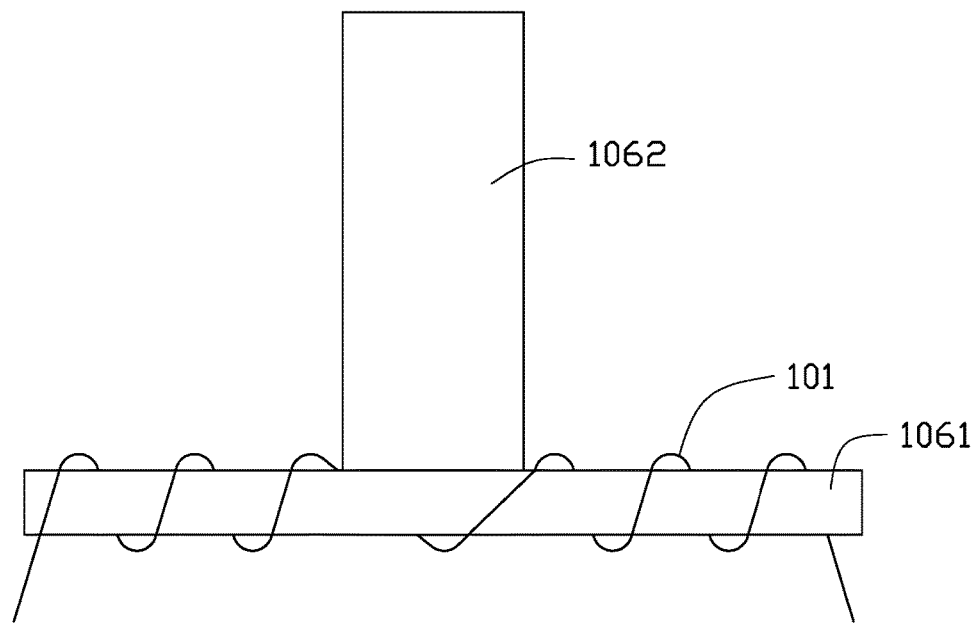
FIG. 5 is a perspective, enlarged view of the liquid guiding wick and the heating device similar to FIG. 4.

Referring to FIGS. 1 to 3, the liquid guiding member 112 is received in one end of the receiving space 1021 of the conductive ring 102. The liquid guiding member 112 comprises a liquid guiding wick 106, a liquid guiding nozzle 107, and a liquid guiding nozzle seat 108. The liquid guiding nozzle seat 108 is integral with the liquid guiding nozzle 107. The liquid guiding wick 106 has two ends, and has an outer surface. Refer to FIG. 3, one end of the liquid guide wick 106, from the liquid guiding nozzle seat 108, reaches the heating device 101, the other end of the liquid guide wick 106 is inserted into the liquid guiding nozzle 107. Refer to FIGS. 4 to 5, the liquid guiding wick 106 comprises a horizontal portion 1061 and a vertical portion 1062. In this exemplary embodiment, the horizontal portion 1061 of the liquid guiding wick 106 is detachably connected to the vertical portion 1062 of the liquid guiding wick 106 (see the FIG. 4). The liquid guiding wick 106 can thus be easily assembled on the liquid guiding nozzle 107, and the horizontal portion 1061 of the liquid guiding wick 106 prevents leakage of the liquid to the atomizing chamber 103. In another exemplary embodiment, the horizontal portion 1061 of the liquid guiding wick 106 and the vertical portion 1062 of the liquid guiding wick 106 can also be integrally formed (see the FIG. 5). The vertical portion 1062 has two ends. One end of the vertical portion 1062 of the liquid guiding wick 106 is attached to or abutted against the horizontal portion 1061 of the liquid guiding wick 106. The other end of the vertical portion 1062 of the liquid guiding wick 106, from the liquid guiding nozzle seat 108, is inserted into the liquid guiding nozzle 107. In this exemplary embodiment, the vertical portion 1062 of the liquid guiding wick 106 is located on a middle portion of the heating device 101. In order to improve the heating efficiency of the heating device 101, the horizontal portion 1061 of the liquid guiding wick 106 is wound around by the heating device 101 (see FIGS. 4 and 5). The heating device 101 is completely within the flow path of the liquid, so the heating effect of the heating device 101 is very efficient in this configuration. The liquid guiding nozzle 107 and the liquid guiding nozzle seat 108 cooperatively define a receiving cavity 113 that is blocked by the liquid guiding wick 106. In this exemplary embodiment, one end of the vertical portion 1062 of the liquid guiding wick 106 blocks a part of the receiving cavity 113. An inner surface of the receiving cavity 113 defines at least one liquid guiding slot 109. The liquid guiding nozzle 107 has a first top end and the first top end of the liquid guiding nozzle 107 has an inclined plane 1071. The inclined plane 1071 has a second top end and the liquid guiding nozzle seat 108 has a bottom end. In this exemplary embodiment, the liquid guiding slot 109 extends from the second top end of the inclined plane 1071 to the bottom end of the liquid guiding nozzle seat 108. In another exemplary embodiment, the liquid guiding slot 109 extends from near the second top end of the inclined plane 1071 to the bottom end of the liquid guiding nozzle seat 108. The at least one liquid guiding slot 109 has an inner surface 1091 spaced apart from an outer surface of the vertical portion 1062 of the liquid guiding wick 106. That is, the inner surface of the at least one liquid guiding slot 109 has a certain distance away from the outer surface of the liquid guiding wick 106. Since the liquid guiding wick 106 does not block the liquid guiding slot 109, the at least one liquid guiding slot 109 can provide a channel for liquid to the heating device 101 through the horizontal portion 1061 of the liquid guiding wick 106. Although the liquid guiding wick 106 helps the uniformity of the liquid flowing to the heating device 101, the liquid flows slowly because of the liquid guiding wick 106. The at least one liquid guiding slot 109 drains the liquid through the liquid guiding slot 109 to improve the flow rate of the liquid. When the heating device 101 is being heated, the heating device 101 has enough liquid to prevent the phenomenon of dry combustion. The liquid guiding nozzle 107 and the liquid guiding nozzle seat 108 are integrally molded. The quantity of the liquid guiding slots 109 relates to the arrangement of the heating device 101 and is a matter of design. When the inner surface of the receiving cavity 113 defines one liquid guiding slot 109, and the heating device 101 is fitted in the atomizing chamber 103 of the support base 100, both ends of the heating device 101 are substantially aligned along a common horizontal axis, that is, both ends of the heating device 101 are substantially coaxial. Since the two ends of the heating device 101 are coaxial, the flow path of the liquid along the surface of the heating device 101 is short. If the atomizing speed is not fast enough for a provision rate of the liquid, there will be leakage, therefore, one liquid guiding slot 109 can meet the requirements, and a universal atomizing head 10 with one liquid guiding slot 109 is suitable for users who use an electronic cigarette that generates a small amount gases. If the inner surface of the receiving cavity 113 defines two or more liquid guiding slots 109, the heating device 101 is situated in the atomizing chamber 103 of the support base 100, one end of the heating device 101 is at a higher elevation than the other end of the heating device 101, i.e. the heating device 101 in the atomizing chamber 103 of the support base 100 is arranged inclined, the reason is that when the heating device 101 is at an angle in the atomizing chamber 103 of the support base 100, the flow path of the liquid is prolonged, and leaks are avoided by increasing the supply amount of the liquid smoke through increasing the number of liquid guiding slots. Thus, the amount of smoke is also improved. A universal atomizing head 10 with two or more liquid guiding slots is suitable for users who use an electronic cigarette that generates a large amount gases. Since the universal atomizing head 10 of the invention can be replaced, the same user can select a specific number of guiding slots 109 of the universal atomizing head 10 as desired. One end of the liquid guiding nozzle seat 108 is inserted into one end of the receiving space 1021 of the conductive ring 102, and the liquid guiding nozzle seat 108 is substantially cylindrical in shape. The outer circumference of the liquid guiding nozzle seat 108 along its axial direction has a truncated section, so the liquid guiding nozzle seat 108 is thereby mounted to the conductive ring 102. A channel is provided between the liquid guiding nozzle seat 108 and the conductive ring 102 for the atomized smoke of the liquid to go through.

Referring to FIGS. 1 to 3, the conductive member 115 is received in the other end of the receiving space 1021 of the conductive ring 102. The conductive member 115 and the conductive ring 102 are connected with the heating device 101 by a plurality of wires. The conductive member 115 includes a conductor 110 and an insulator 111. The conductor 110 is a positive electrode of the universal atomizing head 10. The conductor 110 is mounted on the insulator 111, a second wire is welded to the other end of the heating device 101. The conductor 110 is ring-shaped. The insulator 111 defines an annular fitting groove on an axial end surface for receiving the conductor 110. The insulator 111 is fitted in the receiving space 1021 of the conductive ring 102. A middle portion of the insulator 111 defines an air hole 114 in air communication with the atomizing chamber 103, the air hole 114 has negative pressure of airflow during user inhaling. The conductive member 115 is disposed in the other end of the receiving space 1021 of the conductive ring 102 to increase the compactness of the structure, to reduce the use of parts, and to facilitate installation.

Figure 6:
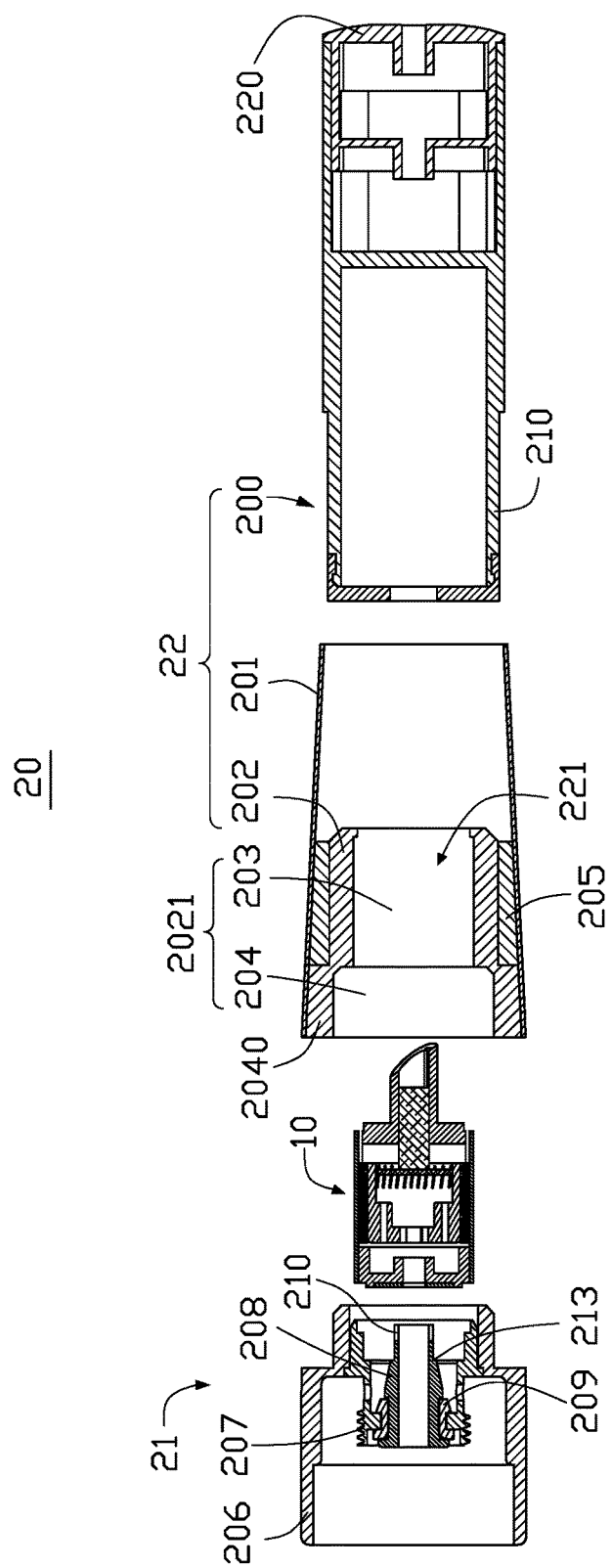
FIG. 6 is a cross-sectional structure view of an atomizer of the present disclosure showing partially disassembled members of the atomizer.

Universal atomizing head 10 is a core of the atomizer, an atomizer structure that is based on universal atomizing head 10 of the present disclosure is described as follows:

Referring to FIG. 6, the atomizer 20 comprises a universal atomizing head 10, a connector 21, and an atomization assembly 22. The universal atomizing head 10 of this exemplary embodiment is described in FIGS. 1 to 3.

To replace the universal atomizing head 10, the atomization assembly 22 defines a space 221 for detachably receiving the atomizing head 10. The atomization assembly 22 includes a cartridge 200, a housing 201, and a first sleeve 202. The cartridge 200 consists of a box 210 for storing the liquid and a spraying piece 220. The box 210 and the spraying piece 220 are connected together and can be directly plugged into the housing 201. The cartridge 200 is connected to one end of the housing 201 and can be plugged to connect with or unplugged to disconnect from the housing 201. The first sleeve 202 is fixed to the other end of the housing 201, and the first sleeve 202 has a stepped bore 2021. The stepped bore 2021 comprises a smaller aperture section 203 and a greater aperture section 204 in air communication with the smaller aperture section 203. The cross-sectional area of the stepped bore 2021 is substantially an inverted T structure. The smaller aperture section 203 of the stepped bore 2021 is defined in the space 221 of the atomization assembly 22. The smaller aperture section 203 is configured for accommodating the replaceable universal atomizing head 10. The replaceable universal atomizing head 10 is received in the space 221, the liquid guiding nozzle 107 is inserted into the box 210 of the cartridge 200 after inserting into the space 221 of the atomization assembly 22. The end of the conductor 110 of the universal atomizing head 10 extends to the greater aperture section 204 of the stepped bore 2021, the conductor 110 is received in a part of the space 221 of the atomization assembly 22. The first sleeve 202 has an annular retaining projection 2040, the greater aperture section 204 of the stepped bore 2021 has a first outer wall, the small aperture section 203 has a second outer wall, the annular retaining projection 2040 is arranged on the first outer wall of the greater aperture section 204, the insulation sleeve 205 is arranged on the second outer wall of the small aperture section 203. When heat generated by the heating device 101 reaches 60 degrees, the heat will be transmitted to the outside of the housing 201. When smoking, a user's hand will grip the electronic cigarette, the insulated sleeve 205 absorbs the heat generated by the heating device 101 to reduce the heat transmitted to the outer wall of the housing 201, and the user will not get burn while using. The housing 201 and the first sleeve 202 are a press fit, therefore the location of the insulated sleeve 205 is limited by the annular retaining projection 2040, and the insulated sleeve 205 is not displaced or slidable on the first sleeve 202.

The connector 21 includes a second sleeve 206, a conductive negative electrode 207, a conductive positive electrode 208, and an insulating member 209. A first end of the second sleeve 206 defines a first outer thread, and one end of the conductive negative electrode 207 located in the second sleeve 206 is provided with a second outer thread. The conductive negative electrode 207 is tube-like, and the conductive negative electrode 207 is a substantially symmetrical structure. The conductive negative electrode 207 has a symmetrical line. A middle portion of the conductive negative electrode 207 defines an alignment hole 213, that is, the conductive negative electrode 207 defines the alignment hole 213 on the symmetrical line. The conductive positive electrode 208 is passed through the alignment hole 213. A notch 210 is defined in the end of the conductive positive electrode 208 for the smoke or gas to pass through. The insulating member 209 is interposed between the conductive positive electrode 208 and the conductive negative electrode 207.

Figure 7:
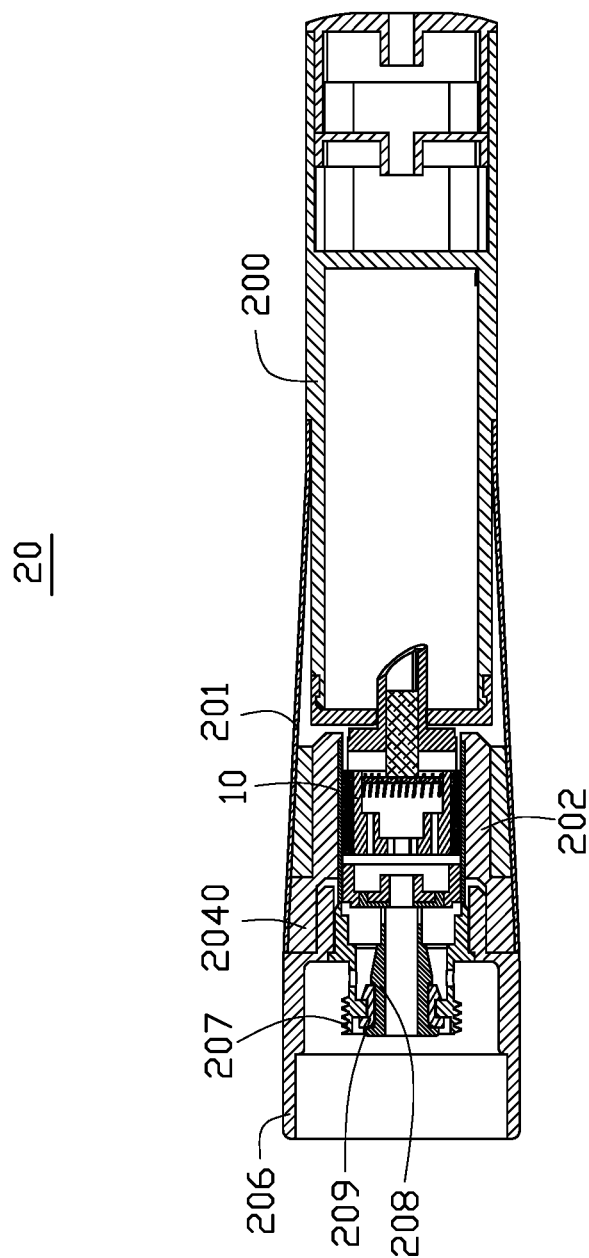
FIG. 7 is a cross-sectional structural view of a first exemplary embodiment of the atomizer in FIG. 6 showing the members of the atomizer assembled.

After the connection of the connector 21 and the atomization assembly 22, the universal atomizing head 10 is in contact with the connector 21 electronically. The conductive negative electrode 207 is in contact with the conductive ring 102 of the universal atomizing head 10, and the conductive positive electrode 208 is in contact with the conductor 110. The connections of the connector 21 and the atomization assembly 22 are as follows:

Referring to FIG. 7, in one exemplary embodiment, the atomization assembly 22 and the connector 21 are connected through a threaded manner. The internal thread is provided on the inner wall of the greater aperture section 204 in the first sleeve 202 of the atomization assembly 22, the first outer end of the connector 21 is on the second sleeve 206. When assembling, the universal atomizing head 10 is first inserted into the small aperture section 203 of the first sleeve 202 of the atomization assembly 22 and then the internal thread of the greater aperture section 204 is connected to the first outer thread of the second sleeve 206.

Figure 8:
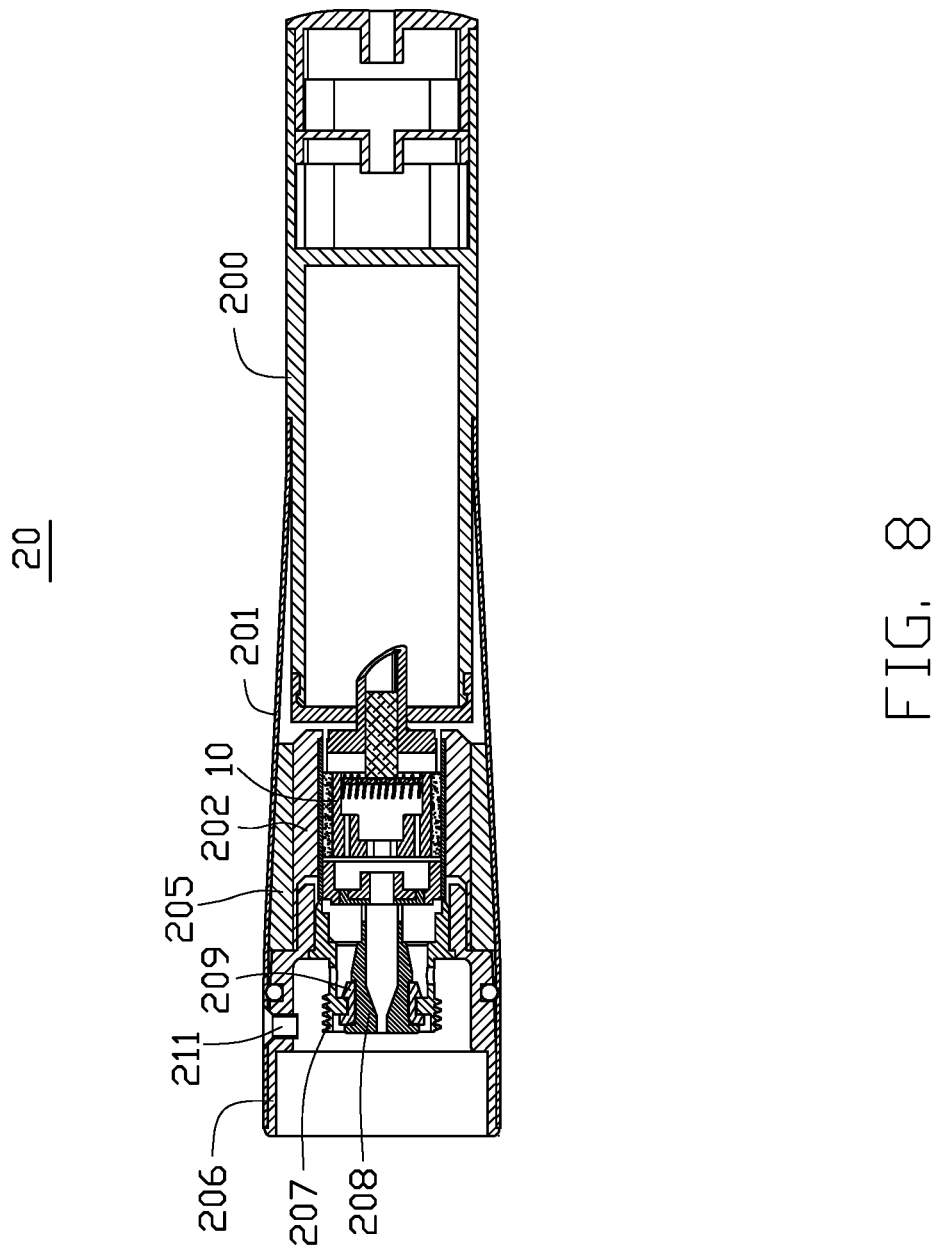
FIG. 8 is a cross-sectional structural view of a second exemplary embodiment of the atomizer in FIG. 6.

With reference to FIG. 8, in another exemplary embodiment, a radial through hole is provided in the circumferential surface of the housing 201 of the atomization assembly 22. A threaded bore is provided on the second sleeve 206 of the connector 21. During assembly, the universal atomizing head 10 is first inserted into the small aperture section 203 of the first sleeve 202 of the atomization assembly 22, then the housing 201 of the atomization assembly 22 is set in the second sleeve 206. Finally, the second sleeve 206 and the housing 201 are screwed together with a screw 211.

Figure 9:
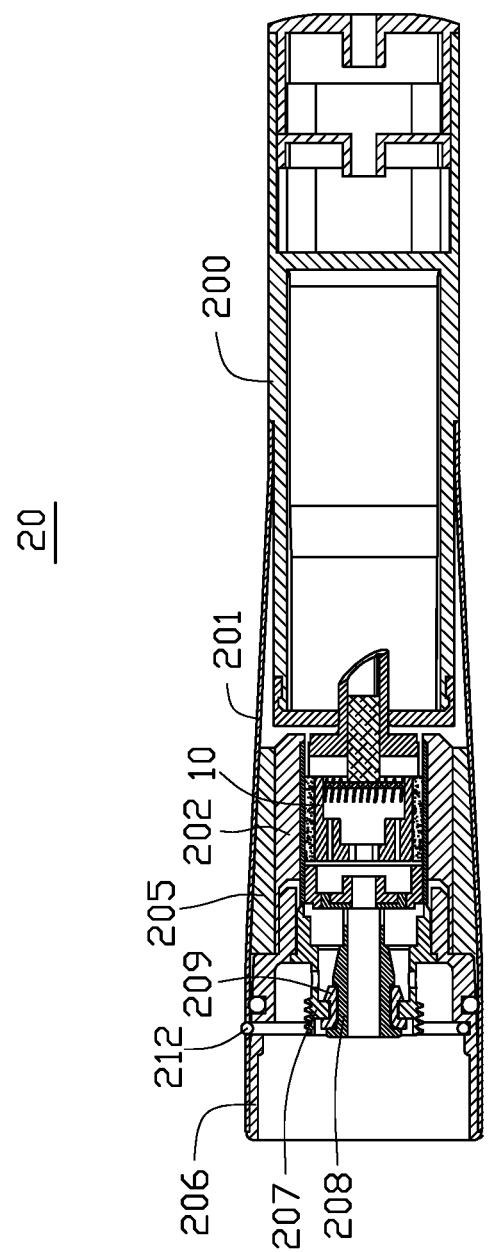
FIG. 9 is a cross-sectional structural view of a third exemplary embodiment of the atomizer in FIG. 6.

Referring to FIG. 9, in another exemplary embodiment, a radial through hole is provided in the circumferential surface of the housing 201 of the atomization assembly 22. A circlip 212 is provided on the second sleeve 206 and the universal atomizing head 10 is first inserted into the small aperture section 203 of the first sleeve 202 of the atomization assembly 22. The housing 201 of the atomization assembly 22 is set in the second sleeve 206, a nub or bump on the circlip 212 is released into the through hole in the housing 201, thus locking the housing 201 and the second sleeve 206.

Figure 10:
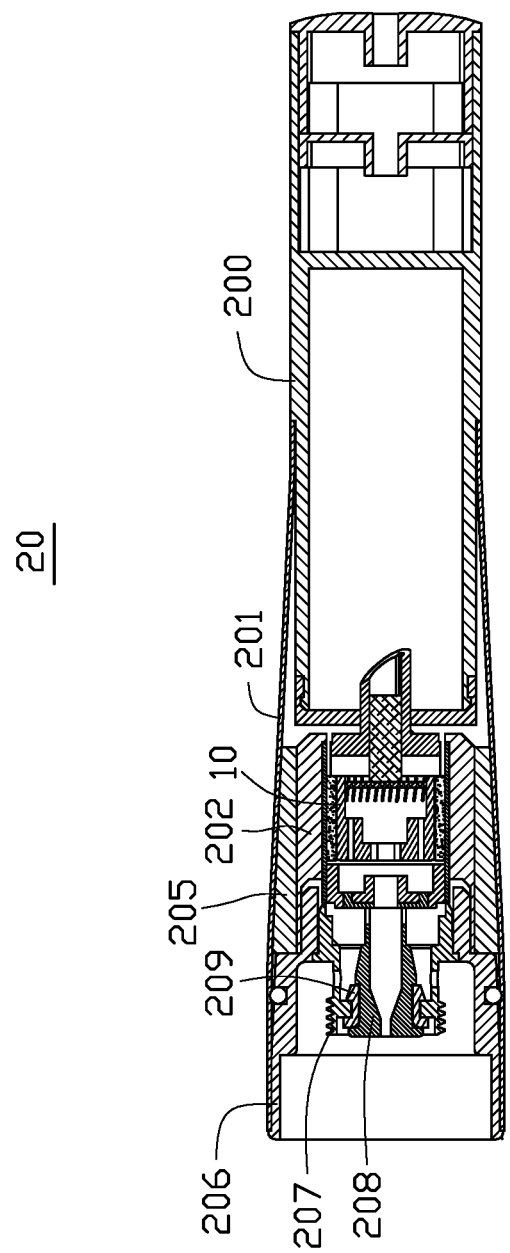
FIG. 10 is a cross-sectional structural view of a fourth exemplary embodiment of the atomizer in FIG. 6.

Referring to FIG. 10, in another exemplary embodiment, the rod housing 201 of the atomization assembly 22 is directly set in the second sleeve 206 of the connector 21 to form a plug connection.

Figure 11:
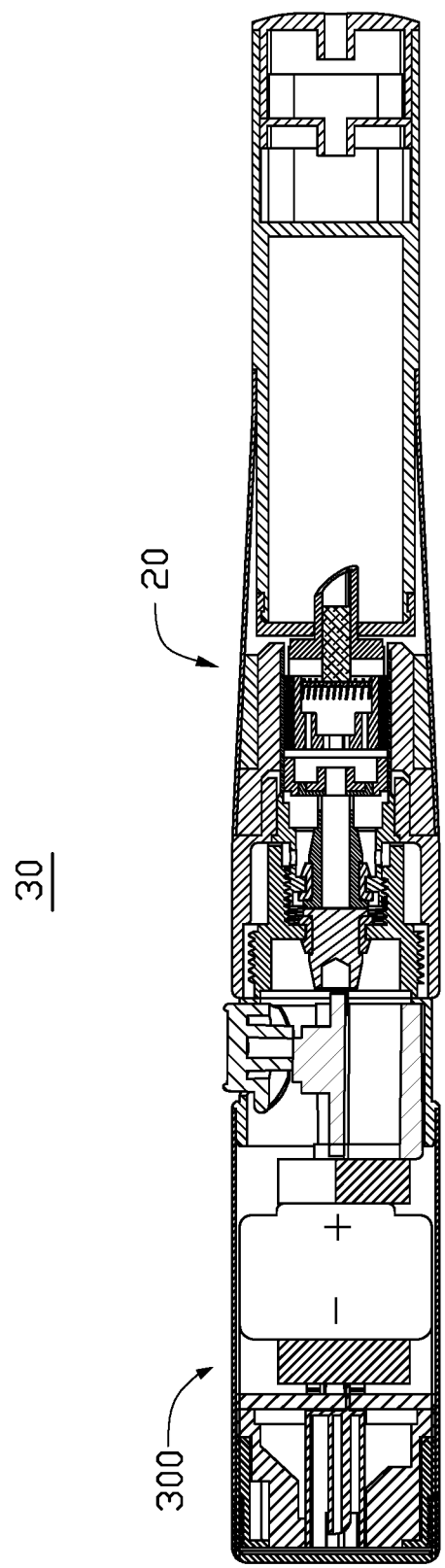
FIG. 11 is a cross-sectional structural view of an electronic cigarette of the present disclosure.
Figure 12:
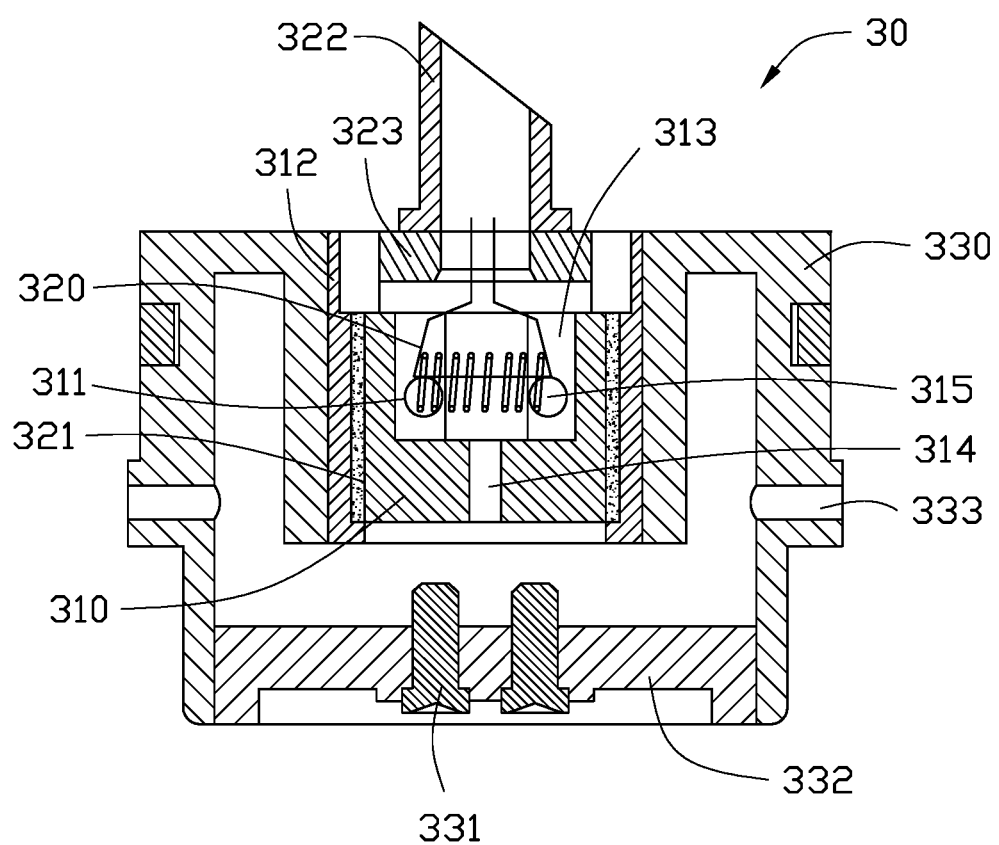
FIG. 12 is a cross-sectional structural view of a prior art atomizer.

Referring to FIG. 11, the electronic cigarette 30 includes the atomizer 20 and battery rod 300. The end of the battery rod 300 comprises an internal thread, and the battery rod 300 connects to the second outer thread of the conductive negative electrode 207, that is the battery rod 300 and the second sleeve 206 are connected through a threaded manner.

The embodiments illustrated and described above are only examples. Many details are often found in the art such as the other features of an atomizing head. Therefore, many such details are neither illustrated nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. A replaceable universal atomizing head, comprising:
   a support base defining an atomizing chamber;
   a heating device, the heating device mounted in the atomizing chamber of the support base; and
   a liquid guiding member, the liquid guiding member comprising:
      a liquid guiding wick, the liquid guiding wick has two ends;
      a liquid guiding nozzle; and
      a liquid guiding nozzle seat, the liquid guiding nozzle seat connected integrally with the liquid guiding nozzle,
   wherein one end of the liquid guide wick extends from the liquid guiding nozzle seat and is positioned on the heating device, the o her end of the liquid guide wick is inserted into the liquid guiding nozzle, the liquid guiding nozzle and the liquid guiding nozzle scat cooperatively define a receiving cavity, the receiving cavity is blocked by the liquid guiding wick on a radial direction of the receiving cavity, the receiving cavity has an inner surface, the inner surface defines at least one liquid guiding slot providing a channel for a liquid to reach the heating device.

2. The replaceable universal atomizing head of claim 1, wherein the at least one liquid guiding slot has an inner surface, the liquid guiding wick has an outer surface spaced apart from the inner surface of the liquid guiding slot.

3. The replaceable universal atomizing head of claim 1, wherein the liquid guiding nozzle has a first top end, the top end of the liquid guiding nozzle has an inclined plane, the incline plane has a second top end, the liquid guiding nozzle seat has a bottom end, the at least one liquid guiding slot extends from the second top end of the inclined plane to the bottom end of the liquid guiding nozzle seat.

4. The replaceable universal atomizing head of claim 1, wherein the liquid guiding wick comprises a horizontal portion and a vertical portion, the vertical portion has two ends, the horizontal portion of the liquid guiding wick is wound around by the heating device, one end of the vertical portion of the liquid guiding wick is attached to or abutted against the horizontal portion of the liquid guiding wick, the other end of the vertical portion of the liquid guiding wick extends from the liquid guiding nozzle seat and is inserted into the receiving cavity of the liquid guiding nozzle.

5. The replaceable universal atomizing head of claim 4, wherein the horizontal portion of the liquid guiding wick is detachably connected to the vertical portion of the liquid guiding wick.

6. The replaceable universal atomizing head of claim 4, wherein the horizontal portion of the liquid guiding wick and the vertical portion of the liquid guiding wick are integrally formed.

7. The replaceable universal atomizing head of claim 1 further comprising a conductive ring, a plurality of wires, and a conductive member, wherein the conductive ring and the conductive member are electrically connected to the heating device by the plurality of wires.

8. The replaceable universal atomizing head of claim 7, wherein the conductive ring defines a receiving space, the support base is in the receiving space and mounted close to a middle portion of the conductive ring, the receiving space has two ends, one end of the liquid guiding nozzle seat is inserted into one end of the receiving space of the conductive ring, and the conductive member is inserted into the other end of the receiving space of the conductive ring.

9. The replaceable universal atomizing head of claim 8, wherein the conductive ring is a negative conductor connected to a first wire, the heating device includes at least one end, and the first wire connected to one end of the heating device is between the support base and the conductive ring.

10. The replaceable universal atomizing head of claim 9, wherein the conductive member comprises a conductor and an insulator, the insulator defining an air hole in air communication with the atomizing chamber; wherein the conductor is fixed on the insulator and welds to a second wire, the second wire is connected to the other end of the heating device; and wherein the insulator having the air hole is fitted in the receiving, space of the conductive ring.

11. The replaceable universal atomizing head of claim 7 further comprising a liquid absorbing member, the liquid absorbing member is between the support base and the conductive ring.

12. The replaceable universal atomizing head of claim 1, wherein the inner surface of the receiving cavity defines one liquid guiding slot; and wherein the heating device is fitted in the atomizing chamber of the support base, and both ends of the heating device are substantially aligned along a common horizontal axis.

13. The replaceable universal atomizing head of claim 1, wherein the inner surface of the receiving cavity defines two or more liquid guiding slots, wherein the heating device is in the atomizing chamber of the support base; wherein the heating device has two ends, the two ends are slanted such that one end of the heating device is at a higher elevation than the other end of the heating device.

14. An atomizer, comprising:
   a replaceable universal atomizing head of claim 1; and
   an atomization assembly defining a space, wherein the replaceable universal atomizing head is detachably received in the space.

15. The atomizer of claim 14, wherein the atomization assembly comprises a cartridge, a housing, and a first sleeve; wherein the housing has two ends, the cartridge is connected to one end of the housing, and the first sleeve is fixed to the other end of the housing; wherein the first sleeve has a stepped bore; the stepped bore comprises a smaller aperture section and a greater aperture section in air communication with the smaller aperture section; wherein the space of the atomization assembly is defined in the smaller aperture section of the stepped bore for accommodating the replaceable universal atomizing head.

16. The atomizer of claim 15, wherein the atomization assembly further comprises an insulation sleeve sleeved on the first sleeve, the first sleeve has an annular retaining projection, the greater aperture section of the stepped bore has a first outer wall, the small aperture section has a second outer wall, wherein the annular retaining projection is arranged on the first outer wall of the greater aperture section, the insulation sleeve is arranged on the second outer wall of the small aperture section, and the insulation sleeve absorbs heat generated by the heating device.

17. The atomizer of claim 14 further comprising a connector detachably connected to the atomization assembly; wherein the connector comprises a second sleeve, a conductive negative electrode, a conductive positive electrode, and a insulating member; wherein a middle portion of the conductive negative electrode defines an alignment hole, the conductive positive electrode is passed through the alignment hole; and wherein the insulating member is interposed, between the conductive positive electrode and the conductive negative electrode.

18. The atomizer of claim 17, Wherein the universal atomizing head further comprising a conductive ring and a conductor; wherein when the connector is connected to the atomization assembly, the conductive negative electrode contacts with the conductive ring of the universal atomizing head, and the conductive positive electrode contacts with the conductor of the universal atomizing head.

19. The atomizer of claim 17, wherein the atomization assembly and the connector are connected through a threaded manner, the atomization assembly and the connector are connected by screw fastening, the atomization assembly and the connector are connected by at least one circlip, or the atomization assembly and the connector being connect through plugs.

20. An electronic cigarette comprising an atomizer of the claim 14, wherein the electronic cigarette further comprises a battery rod, the battery rod is connected to the atomizer through a threaded manner.

\* \* \* \* \*